(12) United States Patent
Kato (10) Patent No.: US 9,284,359 B2
(45) Date of Patent: Mar. 15, 2016

(54) METHOD FOR MASS PREPARATION OF PROTEOGLYCAN

(75) Inventor: Yoji Kato, Hirosaki (JP)

(73) Assignee: Hirosaki University, Aomori (JP)

( * ) Notice: Subject to any disclaimer, the term of this patent is extended or adjusted under 35 U.S.C. 154(b) by 0 days.

(21) Appl. No.: 13/980,415

(22) PCT Filed: Jan. 19, 2012

(86) PCT No.: PCT/JP2012/051120
§ 371 (c)(1),
(2), (4) Date: Jul. 18, 2013

(87) PCT Pub. No.: WO2012/099216
PCT Pub. Date: Jul. 26, 2012

(65) Prior Publication Data
US 2013/0303736 A1 Nov. 14, 2013

(30) Foreign Application Priority Data
Jan. 19, 2011 (JP) ................. 2011-009272

(51) Int. Cl.
*C07K 14/46* (2006.01)
*C07K 14/47* (2006.01)
*A61K 31/737* (2006.01)

(52) U.S. Cl.
CPC ............ *C07K 14/461* (2013.01); *A61K 31/737* (2013.01); *C07K 14/4725* (2013.01)

(58) Field of Classification Search
None
See application file for complete search history.

(56) References Cited

U.S. PATENT DOCUMENTS

| | | | |
|---|---|---|---|
| 3,862,003 | A | 1/1975 | Okuyama et al. |
| 4,350,682 | A | 9/1982 | Balassa |
| 4,473,551 | A | 9/1984 | Schinitsky |
| 6,347,986 | B1 | 2/2002 | Fujii |
| 7,504,115 | B2 * | 3/2009 | Kralovec et al. ........ 424/548 |
| 2002/0045735 | A1 | 4/2002 | Takagaki |
| 2004/0234617 | A1 | 11/2004 | Pang et al. |
| 2005/0070500 | A1 | 3/2005 | Boucher et al. |
| 2005/0130272 | A1 | 6/2005 | Kachi |
| 2006/0258570 | A1 | 11/2006 | Hook et al. |
| 2007/0010430 | A1 | 1/2007 | Sato et al. |
| 2009/0253794 | A1 | 10/2009 | Tomono et al. |
| 2010/0234580 | A1 | 9/2010 | Kudo et al. |
| 2012/0157391 | A1 | 6/2012 | Goto et al. |

FOREIGN PATENT DOCUMENTS

| | | |
|---|---|---|
| CN | 1436537 | 8/2003 |
| CN | 1654670 | 8/2005 |
| CN | 1761686 | 4/2006 |
| CN | 101230369 | 7/2008 |
| CN | 101358220 | 2/2009 |
| EP | 1 570 845 | 9/2005 |
| EP | 1 614 697 | 1/2006 |
| JP | 49-26234 | 3/1974 |
| JP | 2000-175617 | 6/2000 |
| JP | 2001-172296 | 6/2001 |
| JP | 2001-509513 | 7/2001 |
| JP | 2002-69097 | 3/2002 |
| JP | 2003-055255 | 2/2003 |
| JP | 2003-299497 | 10/2003 |
| JP | 2003-300858 | 10/2003 |
| JP | 2005-75740 | 3/2005 |
| JP | 2005-113106 | 4/2005 |
| JP | 2006-143605 | 6/2006 |
| JP | 2007-063177 | 3/2007 |
| JP | 2007-252212 | 10/2007 |
| JP | 2007-262103 | 10/2007 |
| JP | 2007-531509 | 11/2007 |
| JP | 2008-247803 | 10/2008 |
| JP | 2009-173702 | 8/2009 |
| JP | 2011-503170 | 1/2011 |
| JP | 2011-512345 | 4/2011 |
| JP | 2011-524750 | 9/2011 |
| WO | 99/02548 | 1/1999 |
| WO | 2004/067568 | 8/2004 |
| WO | 2004/083257 | 9/2004 |
| WO | 2007/094248 | 8/2007 |
| WO | 2009/063427 | 5/2009 |
| WO | 2009/101194 | 8/2009 |
| WO | 2009-274955 | 11/2009 |
| WO | 2009/155180 | 12/2009 |
| WO | 2011/007885 | 1/2011 |
| WO | 2012/099216 | 7/2012 |
| WO | 2012/099224 | 7/2012 |

OTHER PUBLICATIONS

Mitsui et al., "Salmon cartilage proteoglycan suppresses mouse experimental colitis through induction of Foxp3+ regulatory T cells", Biochemical and Biophysical Research Communications, 2010, 402(2): 209-215.*

(Continued)

*Primary Examiner* — Suzanne M Noakes
(74) *Attorney, Agent, or Firm* — Wenderoth, Lind & Ponack, L.L.P.

(57) ABSTRACT

An object of the present invention is to efficiently extract proteoglycan from aquatic animal tissues. The method of the present invention is a method for extracting proteoglycan from fish cartilage, comprising the step of (A) heating small pieces of frozen fish cartilage in water. This method of the present invention enables easy extraction of proteoglycan from fish cartilage with very high efficiency. In particular, the method of the present invention enables extraction of high-molecular-weight proteoglycan. Further, since in the method of the present invention, extraction is performed using only water, it ensures safety in the extraction and safety of the resulting proteoglycan product, compared with hitherto known extraction methods using organic solvents or acids/alkali. Furthermore, the cumbersome step of removing organic solvents is not necessary in the method of the present invention.

8 Claims, 5 Drawing Sheets

(56) References Cited

OTHER PUBLICATIONS

Hatae et al., "Effects of Vineger-Curing on the Chemical and Physical Properties of the Salmon-Nose-Cartilage", Nippon Shokuhin Kogyo Gakkaishi, vol. 37, No. 7, pp. 505-510, 1990, with English abstract.
U.S. Appl. No. 13/980,429, filed Jul. 18, 2013, Kato.
U.S. Appl. No. 14/046,160, filed Oct. 4, 2013, Goto et al.
U.S. Appl. No. 13/383,987, filed Jan. 13, 2012, Goto et al.
Guo Bin et al., "Isolation, purification, and biological activities of ray cartilage glycosaminoglycans", Chinese Traditional and Herbal Drugs, vol. 37, No. 8, 2006, pp. 1210-1214, with English abstract.
Supplementary European Search Report dated Jan. 30, 2013 in corresponding European Patent Application No. 10 799943.5.
International Search Report and partial English translation of Written Opinion of the International Searching Authority issued Apr. 3, 2012 and International Preliminary Report on Patentability issued Jul. 23, 2013 in International (PCT) Application No. PCT/JP2012/051131.
International Search Report and English translation of Written Opinion of the International Searching Authority issued Sep. 7, 2010 and International Preliminary Report on Patentability issued Feb. 7, 2012 in International (PCT) Application No. PCT/JP2010/062125.
International Search Report issued Mar. 19, 2012 in International (PCT) Application No. PCT/JP2012/051120.
Kralovec et al., "Immunomodulating principles from shark cartilage Part 1. Isolation and biological assessment in vitro", International Immunopharmacology, vol. 3, 2003, pp. 657-669.
Supplementary European Search Report dated Oct. 20, 2014 issued in European Patent Application No. 12737027.8.
Goto et al., "Anti-aging effects of high molecular weight proteoglycan from salmon nasal cartilage in hairless mice", International Journal of Molecular Medicine, vol. 29, No. 5, May 2012, pp. 761-768.
Goto et al., "Anti-aging effects of extracts prepared from salmon nasal cartilage in hairless mice", Molecular Medicine Reports, vol. 4, May 23, 2011, pp. 779-784.
Roth et al., "Intra-articular injections of high-molecular-weight hyaluronic acid have biphasic effects on joint inflammation and destruction in rat antigen-induce arthritis", Arthritis Research & Therapy, vol. 7, No. 3, Mar. 31, 2005, pp. R677-R686.
U.S. Office Action dated Jul. 16, 2014 issued in U.S. Appl. No. 14/046160.
Kalman, D. et al., "Effect of a natural extract of chicken combs with a high content of hyaluronic acid (Hyal-Joint) on pain relief and quality of life in subjects with knee osteoarthritis: a pilot randomized double-blind placebo-controlled trial", Nutrition Journal, 2008. 7:3, pp. 1-9.
Fujita, S. et al., "Demonstration of EGF-like activity in salmon cartilage proteoglycan", Poster Presentation 2P-0051.
"Causing of Aging Skin from Aging Skin Net", from AgingSkinNet, retrieved on May 12, 2014, from URL <http://www.skincarephysicians.com/agingskinnet/basicfacts.html>.
U.S. Office Action dated Nov. 5, 2014 issued in related U.S. Appl. No. 14/046,160.
Takahashi, "Sake Binankotsu Proteoglycan no Kansetsutsu Oyobi Nankotsu Taisha ni Taisuru Yuyosei", Food Style 21, vol. 15, No. 10, 2011, pp. 52-54, cited in ISR.
Kakizaki et al., "Identification of proteoglycan from salmon nasal cartilage", Archives of Biochemistry and Biophysics, vol. 506, No. 1, Nov. 5, 2010, pp. 58-65.
Sugawara et al., "Sake Binankotsu Yurai Proteoglycan Natrium no Hinshitsu Hoji Gijutsu no Kaihatsu (Minkan To Kyodo Kenkyuhi)", Hokkai Doritsu Kushiro Suisan Shikenjo Jigyo Hokokusho, vol. 2003, 2005, p. 106, cited in ISR.
International Search Report issued Aug. 20, 2013, in International (PCT) Application No. PCT/JP2013/070134.
US Office Action dated Jan. 15, 2015 issued in corresponding U.S. Appl. No. 13/980,429.
U.S. Office Action dated Jun. 17, 2015, issued in related U.S. Appl. No. 14/046,160.
U.S. Office Action dated Jul. 10, 2015, issued in related U.S. Appl. No. 13/980,429.
Nagatsuka et al., "Radical scavenging activity of 'Nikogori' gelatin gel food made from head, bone, skin, tail and scales of fishes measured using the chemiluminescence method", International Journal of Molecular Medicine, 2007, vol. 20, pp. 843-847.
Extended European Search Report dated Oct. 14, 2015, issued in European Patent Application No. 13823573.4.
Hiroshi Sashinami, et al., "Salmon cartilage proteoglycan modulates cytokine responses to *Escherichia coli* in mouse macrophages", Biochemical and Biophysical Research Communications, 2006, vol. 351, No. 4, pp. 1005-1010.
Toshihito Mitsui, et al., "Salmon cartilage proteoglycan suppresses mouse experimental colitis through induction of Foxp3+ regulatory T cells", Biochemical and Biophysical Research Communications, 2010, vol. 402, No. 2, pp. 209-215.
Sayuri Yoshimura, et al., "Attention of Collagen-Induced Arthritis in Mice by Salmon Proteoglycan", BioMed Research International, 2014, vol. 171, No. 11, pp. 6173-6179.
Yota Tatara, et al., "Epiphycan from salmon nasal cartilage is a novel type of large leucine-rich proteoglycan", Glycobiology, 2013, vol. 23, No. 8, pp. 993-1003.
S. Nuka, et al., "Phenotypic characterization of epiphycan-deficient and epiphycan/biglycan double-deficient mice", Osteoarthritis and Cartilage, 2010, vol. 18, No. 1, pp. 88-96.

\* cited by examiner

*Value per gram of frozen salmon nasal cartilage

METHOD FOR MASS PREPARATION OF PROTEOGLYCAN

TECHNICAL FIELD

The present invention relates to a method for preparing proteoglycan. More specifically, the present invention relates to, in particular, a proteoglycan extraction method enabling mass preparation of high-molecular-weight proteoglycan with high efficiency.

BACKGROUND ART

Proteoglycan is one of the major biological macromolecules for forming the substrate of the extracellular matrix of connective tissue, as are collagen and others. Proteoglycan was hitherto obtained by being extracted and isolated from mammal cartilage (in particular, bovine cartilage). However, ever since the occurrence of bovine spongiform encephalopathy (BSE) was reported, the use of bovine cartilage has been avoided. Thus, there has been a need for an alternative source of proteoglycan, and a production method for the alternative source. In addition, since the production cost for proteoglycan is very high due to the complexity of the existing proteoglycan extraction step and the low yield, industrial application of proteoglycan has not been fully accomplished. Thus, there has been a need for a simpler method ensuring a greater yield.

As an alternative source for proteoglycan, aquatic animal tissue is attracting attention. Therefore, there have been attempts to extract proteoglycan from cartilage of aquatic animals, such as whales and sharks. However, due to catch restrictions placed on these aquatic animals, it has been difficult to produce a large amount of proteoglycan. Moreover, the extraction and isolation of proteoglycan is complicated, and some solvents, etc., used for extraction have relatively high toxicity.

Under such circumstances, there have been attempts to extract proteoglycan from the large amount of discarded aquatic animal tissues (e.g., salmon nasal cartilage). Patent Document 1 discloses a method for producing a composition (nasal cartilage powder) containing proteoglycan from salmon nasal cartilage. In particular, since proteoglycan derived from salmon nasal cartilage is assumed to have an effect for treating or preventing inflammatory enteric diseases, demand for proteoglycan is increasing. However, the method of Patent Document 1 cannot ensure sufficiently high production efficiency; thus, the method has yet to be improved in terms of efficiency.

CITATION LIST

Patent Documents

Patent Document 1: JP2009-173702A

SUMMARY OF INVENTION

Technical Problem

An object of the present invention is to efficiently extract proteoglycan from aquatic animal tissues.

Solution to Problem

Surprisingly, the inventors of the present invention found that a method of freezing fish cartilage, pulverizing the cartilage into small pieces, and heating the pieces in water enables extraction of proteoglycan with high efficiency. After several attempts to further improve the method, the inventors completed the present invention.

Specifically, the present invention encompasses the proteoglycan extraction methods (i.e., proteoglycan production methods) and methods for improving efficiency in proteoglycan extraction set forth in the following Items 1 to 11.

Item 1

A method for extracting proteoglycan from fish cartilage, comprising the step of (A) heating small pieces of frozen fish cartilage in water.

Item 2

The method according to Item 1, wherein each small piece of frozen fish cartilage is 0.001 to 0.5 g.

Item 3

The method according to Item 1 or 2, wherein the small pieces of frozen fish cartilage are obtained by freezing fish cartilage and then pulverizing the frozen fish cartilage.

Item 4

The method according to Item 3, wherein the fish cartilage is defatted fish nasal cartilage.

Item 5

The method according to any one of Items 1 to 4, wherein the extracted proteoglycan contains proteoglycan having a molecular weight of not less than 900,000 ($90 \times 10^4$).

Item 6

The method according to any one of Items 1 to 5, wherein the heating in Step (A) is performed for more than 3 hours.

Item 7

The method according to any one of Items 1 to 6, wherein the temperature of water used in the heating in Step (A) is not less than 80° C.

Item 8

The method according to any one of Items 1 to 7, wherein the mass ratio of all the small pieces of frozen fish cartilage to water is 1:1 to 1:10.

Item 9

The method according to any one of Items 1 to 8, wherein the heating in Step (A) is continued until the mass of a residue collected after the heating is equal to or less than the mass of the heated small pieces of frozen fish cartilage.

Item 10

The method according to Item 9, wherein the residue collected after the heating is a precipitate obtained by centrifugation at 5000 rpm, 4° C., for 20 minutes.

Item 11

A method for increasing efficiency in proteoglycan extraction from fish cartilage, comprising the step of heating small pieces of frozen fish cartilage in water.

Advantageous Effects of Invention

The proteoglycan extraction method of the present invention enables easy extraction of proteoglycan from fish cartilage with very high efficiency. In particular, the proteoglycan extraction method of the present invention enables extraction of high-molecular-weight proteoglycan. Further, since in the extraction method of the present invention, extraction is performed by using only water, the method ensures safety in the extraction and safety of the resulting proteoglycan product, compared with hitherto known extraction methods using organic solvents or acids/alkali. Furthermore, the step of removing the organic solvents is usually cumbersome, but this step is not necessary in the extraction method of the present invention.

DESCRIPTION OF EMBODIMENTS

The present invention is described in more detail below. The term "mass" in this specification is equivalent to "weight".

The proteoglycan extraction method of the present invention is a method for extracting proteoglycan from fish cartilage. The method comprises the step of (A) heating small pieces of frozen fish cartilage in water.

The fish cartilage is cartilage obtained from fish, preferably from *Oncorhynchus* (Salmonidae). Examples of the fish include trout (humpback salmon, cherry salmon, satsukimasu salmon, etc.), salmon (chum salmon, sockeye salmon, silver salmon, chinook salmon, steelhead, etc.), shark, and cod. Salmon and trout are particularly preferable. The cartilage to be used is not particularly limited; however, head cartilage, in particular, nasal cartilage, is preferable. Moreover, since fish heads are usually discarded when fish is processed into food products, the cost of fish heads is low, and a large amount of fish heads can be stably supplied.

The small frozen pieces of fish cartilage can be obtained either by (i) freezing fish cartilage and then pulverizing it into small pieces or (ii) pulverizing fish cartilage into small pieces and then freezing it. It is also possible to use (iii) frozen fish cartilage itself. The small frozen pieces of fish cartilage obtained by method (i) are particularly preferable in the present invention. The present invention also encompasses a proteoglycan extraction method further comprising, before Step (A), the steps of (α) freezing fish cartilage and/or (β) pulverizing fish cartilage into small pieces.

The freezing method is not particularly limited, and any known freezing method can be used. For example, a method of storing fish cartilage in a freezer at about −20 to −80° C. for about 24 to 72 hours can be used.

The pulverization may be performed using a known method. For example, the pulverization of fish cartilage (preferably frozen fish cartilage) into powder may be performed using known devices such as a blender or a mill. The pulverization is preferably performed at a low temperature (e.g., not more than 4° C.).

Each small piece of frozen fish cartilage is preferably about 0.001 to 0.5 g, more preferably about 0.005 to 0.3 g, further preferably about 0.001 to 0.1 g. The pulverization of fish cartilage into small pieces is preferably performed in a manner enabling production of such small pieces of frozen fish cartilage. Further, if the small pieces of frozen fish cartilage having a weight in the above range are obtained after freezing fish cartilage, it is not necessary to perform the pulverization. Although it is not particularly limited, the small pieces of frozen fish cartilage having a weight in the above range are preferably not less than 50 mass %, more preferably not less than 70 mass %, further preferably not less than 90 mass % among all the small pieces of frozen fish cartilage subjected to heating. This ratio is found by randomly selecting 20 pieces from all the small pieces of frozen fish cartilage subjected to heating, measuring the mass of each of the 20 small pieces, and calculating the proportion (%) of the pieces that have a weight in the above range in the 20 small pieces. "All the small pieces" herein refers to a group of small pieces, i.e., an collection consisting of multiple small pieces.

Although it is not particularly limited thereto, defatted fish cartilage is preferably used. By using defatted fish cartilage, a highly purified proteoglycan-containing fish cartilage extract that incorporates less lipid can be obtained. The defatting may be performed by using a known method. For example, a method of running fish cartilage under water (e.g., tap water) for about 1 to 24 hours can be performed. Preparation of fish cartilage can be performed using a known method, including a method of immersing fish tissues (preferably a fish head) in water for about 1 to 24 hours to make the tissues swell, and removing tissues other than cartilage (preferably nasal cartilage), and a method of thawing a frozen salmon head, then immediately separating the nasal cartilage and running the nasal cartilage under water for about 1 to 24 hours, thereby washing and defatting the cartilage. If the cartilage has residual flesh, it is preferable to remove the flesh with tweezers or the like.

The proteoglycan extracted by the proteoglycan extraction method of the present invention contains a high-molecular-weight proteoglycan. The inventors of the present invention suggest that the effect of treating and preventing inflammatory enteric diseases of the proteoglycan increases as the molecular weight of proteoglycan increases. Thus, the present invention, which enables production of high-molecular-weight proteoglycan, is advantageous also in this regard. The term "high-molecular-weight proteoglycan" used herein specifically refers to a proteoglycan having a molecular weight of not less than 900,000 ($90 \times 10^4$), preferably not less than 1,000,000 ($100 \times 10^4$), more preferably not less than 1,200,000 ($120 \times 10^4$). The present invention is assumed to be capable of producing a proteoglycan having a molecular weight of not less than 2,500,000 ($250 \times 10^4$), or even 5,000,000 ($500 \times 10^4$). The preferable high-molecular-weight proteoglycan is determined by subjecting the proteoglycan-containing extract obtained by the proteoglycan extraction method of the present invention to gel filtration chromatography under the following conditions, determining the uronic acid amount (reflecting the proteoglycan amount) in each fraction by using a carbazole-sulfuric acid method, creating a chromatogram based on the determined uronic acid amounts, and confirming that the peak of the chromatogram is equal to or more than the above range of molecular weight (not less than 900,000 (90×10$^4$), preferably not less than 1,000,000 (100×10$^4$), more preferably not less than 1,200,000 (120× 10$^4$)). Such a chromatogram based on the uronic acid amount may be hereinafter referred to as "proteoglycan uronic acid amount chromatogram. Further, it is also possible to make a chromatogram (reflecting the protein amount) based on the absorbencies by measuring the absorbencies of the fractions at 280 nm, and then finding the relative values of the protein amounts based on the measurement results (i.e., the measurement values are assumed to be values that reflect the protein amounts). Hereinafter, such a chromatogram may be referred to as "proteoglycan protein amount chromatogram".

Gel Filtration Chromatography

Column: Sepharose CL-4B packed column (1-cm dia.×38.5 cm column packed with Sepharose CL-4B as a carrier. Sepharose CL-4B is available from, for example, GE Healthcare and other companies.

Sepharose CL-4B, CAS registry No. 61970-08-9, is a 4% crosslinked agarose with a particle size of 40 to 165 μm (measured by the laser diffraction scattering method).)

Buffer: 0.1 M phosphate buffer (pH of 7.0, containing 0.2 M NaCl) Amount of fraction: 1 mL/tube Molecular weight analytical curve: An analytical curve for use is prepared by subjecting the various dextran molecular weight markers described below to gel filtration chromatography under the same conditions as described above and measuring the absorbency (which reflects the amount of dextran) of each fraction by the phenol-sulfuric acid method, which is a well-known method for detecting sugar chains.

Dextran Molecular Weight Markers

| | |
|---|---|
| Dextran Standard 1,400,000 (Sigma) | 1400 kDa |
| Dextran Standard 670,000 (Sigma) | 670 kDa |
| Dextran Standard 410,000 (Sigma) | 410 kDa |
| Dextran Standard 270,000 (Sigma) | 270 kDa |

Quantification of dextran (absorbency measurement) is performed as follows, according to the method described in Hodge, J. E., and Hofreiter, B. T., Method in Carbohydrate Chemistry, 1, 338 (1962).

[1] 500 μl of a sample aqueous solution or a standard monosaccharide (mannose) aqueous solution is placed in a 105×15 mm test tube.

[2] 500 μl of a phenol reagent (5 v/v % aqueous phenol solution) is added thereto, and the mixture is stirred.

[3] 2.5 mL of concentrated sulfuric acid is added thereto, and immediately the mixture is stirred vigorously for 10 seconds.

[4] The mixture is left to stand for 20 minutes or more at room temperature.

[5] The absorbency at 490 nm is measured with a spectrophotometer.

The carbazole-sulfuric acid method refers to a well-known method performed by adding a carbazole solution, which is a color component of uronic acid (glucuronic acid (Glc A), iduronic acid, etc.), to a measurement specimen, and measuring the absorbency by using a spectrophotometer. An analytical curve is plotted using the glucuronic acid standard solution having a specific concentration, thereby finding the glucuronic acid content in the specimen. More specifically, the carbazole-sulfuric acid method is performed as follows. 2.5 ml of a reagent obtained by dissolving 0.95 g of sodium borate decahydrate in 100 ml of a concentrated sulfuric acid is placed in a test tube and ice-cooled. 0.5 ml of a test object (preferably containing 2 to 20 μg of uronic acid) is gently layered thereon. The mixture is stirred well while being ice-cooled, thereby keeping it at room temperature or below. After the test tube is covered with a glass ball, the test tube is heated in a boiling water bath for 10 minutes, followed by water cooling to decrease the temperature to room temperature. Then, 0.1 ml of a reagent obtained by dissolving 125 mg of carbazole in 100 ml of anhydrous methyl alcohol is added and mixed therewith, and the mixture is heated in a boiling water bath for 15 minutes. Thereafter, the mixture is water-cooled to room temperature, and the absorbency at 530 nm is measured. In the blank test, 0.5 ml of distilled water is used. Simultaneously, an analytical curve is plotted using a glucuronic acid.

The heating in Step (A) is performed to the extent in which the effect of the present invention is ensured. Although the heating conditions are not limited insofar as the effect of the present invention is obtained, an example of the heating conditions is as follows. Although it depends on the heating temperature, the heating time is preferably more than 3 hours, more preferably not less than 3.5 hours, further preferably not less than 4 hours. Although it depends on the heating time, the temperature of water used for the heating is preferably not less than 80° C., more preferably not less than 90° C., further preferably a boiling temperature (100° C. or more under 1 atmospheric pressure).

Further, although the amount of small pieces of frozen fish cartilage to be subjected to heating and the water amount may be suitably determined, it is preferable to immerse all the small pieces in water. Specifically, the mass ratio of all the small pieces to water (all the small pieces:water) is preferably about 1:1 to 1:10.

When the small pieces of frozen fish cartilage are immersed in water, the small fish cartilage pieces swell as the water permeates into the pieces. Further, during the heating, the small swollen fish cartilage pieces are gradually softened and deformed, and finally become a thick fluid partially dissolved in water. Therefore, the appropriate heating level may be determined according to the mass of the small swollen fish cartilage pieces after the heating (i.e., the residue remaining after the heating). More specifically, in the present invention, it is preferable to perform the heating until the mass of all the small swollen fish cartilage pieces (i.e., residue) resulting from the heating falls below the total mass of the small pieces of frozen fish cartilage subjected to the heating; more preferably, the heating is performed until the mass of all the small swollen fish cartilage pieces (i.e., residue) resulting from the heating falls to 70% or less, more preferably 50 mass % or less, of the total mass of the small pieces of frozen fish cartilage used for the heating.

The expression "all the small swollen fish cartilage pieces" (i.e., residue) herein refers to a precipitate obtained by 20-minute centrifugation at 5000 rpm and 4° C. (the precipitate obtained by removing the solution after the centrifugation).

The liquid portion (water) of the product obtained after Step (A) contains a large amount of proteoglycan. Therefore, by collecting the liquid portion, it is possible to obtain a proteoglycan-containing extract. The collection of the liquid portion is performed by removing the supernatant through, for example, a centrifugation treatment (preferably the centrifugation under the above conditions). The liquid (supernatant) may be used as it is, or it may further be purified by a known method. It is also possible to concentrate the liquid by distillation, freeze-drying, or the like. It is also possible to powderize the liquid according to the freeze-drying method or the spray drying method. The other processes may also be performed insofar as the effects of the present invention are not impaired. The proteoglycan thus obtained may be used as, for example, materials for food, cosmetics, medicinal products, and the like.

The usage of the proteoglycan obtained by the method of the present invention is not limited; however, since the proteoglycan provides the aforementioned effects, the proteoglycan of the present invention is suitable for compositions for external use or oral compositions. More specifically, a preferable usage is a composition for external use or an oral composition containing the proteoglycan obtained by the method of the present invention. The proteoglycan-containing extract may be used directly as a composition for external use or as an oral composition. The composition for external use or an oral composition may be used, for example, as a medicinal composition, a quasi-drug composition, a cosmetic composition, or a food composition. These may be produced by a standard method using the proteoglycan obtained by the method of the present invention. They are particularly useful for products in the oral-care industry, cosmetics industry, and food and drink industry.

The oral compositions containing the proteoglycan-containing extract obtained by the method of the present invention (which may be hereinafter referred to as oral compositions of the present invention) used in the oral-care industry may be the proteoglycan-containing extract itself, or a composition produced by appropriately combining the proteoglycan-containing extract with other components (e.g., abrasives, foaming agents, cleaners, surfactants, wetting agents, pH adjusters, thickeners, flavoring agents, and the like) generally used for oral compositions. Examples of the oral composition products include paste agents, ointments, gels, embrocations, sprays, supplements, liquids, mouthwashes, pasta, chewing gum, troches, and tablets, which may be manufactured by standard methods.

Such oral compositions of the present invention can be preferably used for alleviation of inflammation in oral tissues, or anti-aging in oral tissues. More specifically, the oral compositions of the present invention encompass an inflammation alleviation oral composition and an anti-aging oral composition.

The cosmetic composition (hereinafter may be referred to as "cosmetic composition of the present invention") containing the proteoglycan-containing extract obtained by the method of the present invention may be the proteoglycan-containing extract of the present invention itself, or a composition produced by appropriately combining the proteoglycan-containing extract with cosmetically acceptable media, bases, carriers, additives, or other cosmetically acceptable components or materials using a standard method. More specifically, the cosmetic compositions produced by incorporating the proteoglycan-containing extract of the present invention include emulsions, lotions, creams, serums, foundation, face masks, and sunscreens. Such a cosmetic composition of the present invention may be preferably used for alleviation of inflammation or for anti-aging. Examples of preferable usages include compositions for sun protection, sunburn care, moisturizing and anti-aging of the skin (e.g., prevention or alleviation of dry skin, rough skin, facial wrinkles, or sagging skin).

The food and beverage compositions (food and beverages) containing the proteoglycan-containing extract obtained by the method of the present invention (which may be hereinafter referred to as food and beverage compositions of the present invention) used in the food industry may be the proteoglycan-containing extract itself, or a composition produced by appropriately combining the proteoglycan-containing extract with bases, carriers or additives that are acceptable in terms of food hygiene, or other components or materials that are used for food and beverages. Examples of these include processed food and beverages containing the proteoglycan-containing extract with claimed effects of moisturizing and anti-aging of the skin (e.g., prevention or alleviation of dry skin, rough skin, facial wrinkles, or sagging skin), health food (food with nutrient function claims, food for specific health uses, etc.), dietary supplements, beauty food, and food for patients. Moreover, the present invention also includes moisturizers and skin anti-aging agents formed of the aforementioned food and beverage compositions of the present invention. The moisturizers and skin anti-aging agents may be supplied in the forms of drinks, pills, tablets, capsules, granules, jelly, troches, or the like for cosmetic or skin anti-aging purposes (e.g., prevention or alleviation of dry skin, rough skin, facial wrinkles, or sagging skin).

The amount of the proteoglycan-containing extract contained in the oral compositions, cosmetic compositions, or food or beverage compositions of the present invention is, for example, but not limited to, generally 0.001 to 100 mass %, preferably 0.01 to 95 mass %, based on the entire composition.

The proteoglycan-containing extract obtained by the proteoglycan extraction method of the present invention contains a proteoglycan extracted with high efficiency. More specifically, based on the uronic acid amount (i.e., based on the uronic acid amount found by the carbazole-sulfuric acid method), not less than 60 mass %, preferably not less than 70 masse, more preferably not less than 80 mass %, further preferably not less than 90 mass % of the proteoglycan contained in the small pieces of frozen fish cartilage used for the extraction can be extracted by the method of the present invention. Further, as described above, the proteoglycan obtained by the proteoglycan extraction method of the present invention is a high-molecular-weight proteoglycan. More specifically, the proteoglycan-containing extract obtained by the proteoglycan extraction method of the present invention preferably contains a proteoglycan having a molecular weight of not less than 900,000 ($90 \times 10^4$) (more preferably a molecular weight of not less than 1,000,000 ($100 \times 10^4$), further preferably a molecular weight of not less than 1,200,000 ($120 \times 10^4$)). The proteoglycan having the molecular weight of not less than the above range is preferably not less than 60 mass %, more preferably not less than 70 mass %, further preferably not less than 80 mass %, further more preferably not less than 90 mass % of all the proteoglycan extracted. The proportion can be found from a peak area in the aforementioned proteoglycan uronic acid amount chromatogram by calculating a proportion of the area of a proteoglycan having a molecular weight of not less than the above range. More specifically, the proportion can be found by calculating a proportion of the area of a proteoglycan having a molecular weight of not less than the above range based on the entire peak area of the proteoglycan uronic acid amount chromatogram.

Further, the present invention also encompasses a method for increasing efficiency in proteoglycan extraction from fish cartilage, comprising the step of heating small pieces of frozen fish cartilage in water. In this method, the preparation of small pieces of frozen fish cartilage, the heating, the measurement of proteoglycan extraction efficiency, and the like may be performed using the aforementioned methods and conditions.

According to the methods described above, the present invention enables easy extraction of proteoglycan from fish cartilage with very high efficiency, as well as increasing efficiency in proteoglycan extraction from fish cartilage. In particular, the method of the present invention enables extraction of high-molecular-weight proteoglycan. Although a restrictive interpretation is not desired, the present invention succeeded in such a highly efficient extraction of proteoglycan (in particular, a high-molecular-weight proteoglycan) not only by using small pieces of fish cartilage, but also by pulverizing frozen fish cartilage into small pieces. More specifically, in this method, the function of the enzyme (in particular, the enzyme for decomposing proteoglycan) contained in the bone tissue is assumed to be suppressed, and the heating process is assumed to further deactivate the enzyme. In this view, it is further assumed that the fish cartilage is preferably handled at a low temperature, and that the water used for extraction is preferably heated to a high temperature at the time of addition of the small pieces of frozen fish cartilage.

EXAMPLES

Figure 1A:
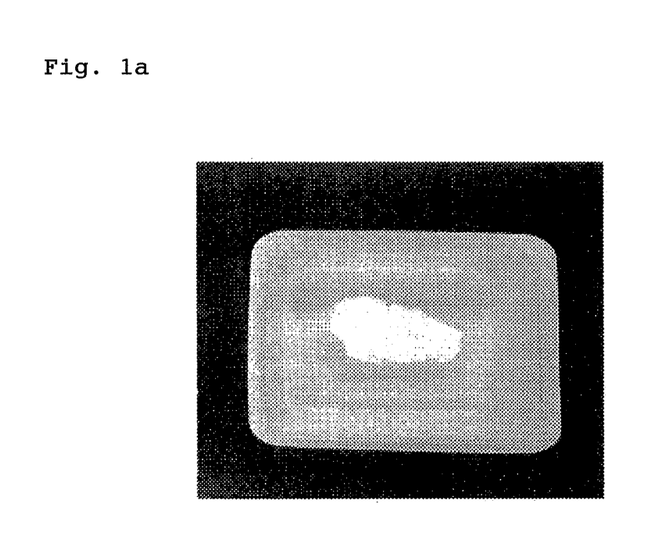
FIG. 1a is a photo of a frozen salmon nasal cartilage block placed in a tray.
Figure 1B:
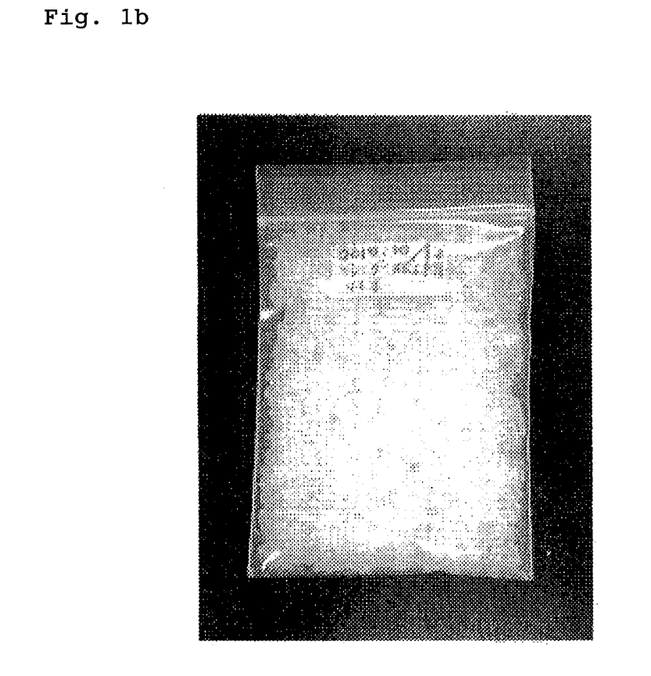
FIG. 1b is a photo of small pieces of frozen salmon nasal cartilage placed in a plastic bag.
Figure 1C:
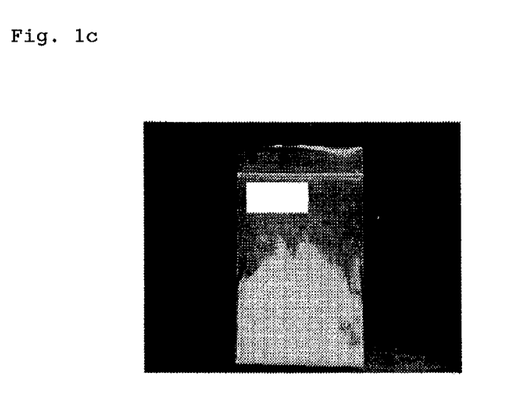
FIG. 1c is a photo of defatted salmon nasal cartilage powder placed in a plastic bag.
Figure 2:
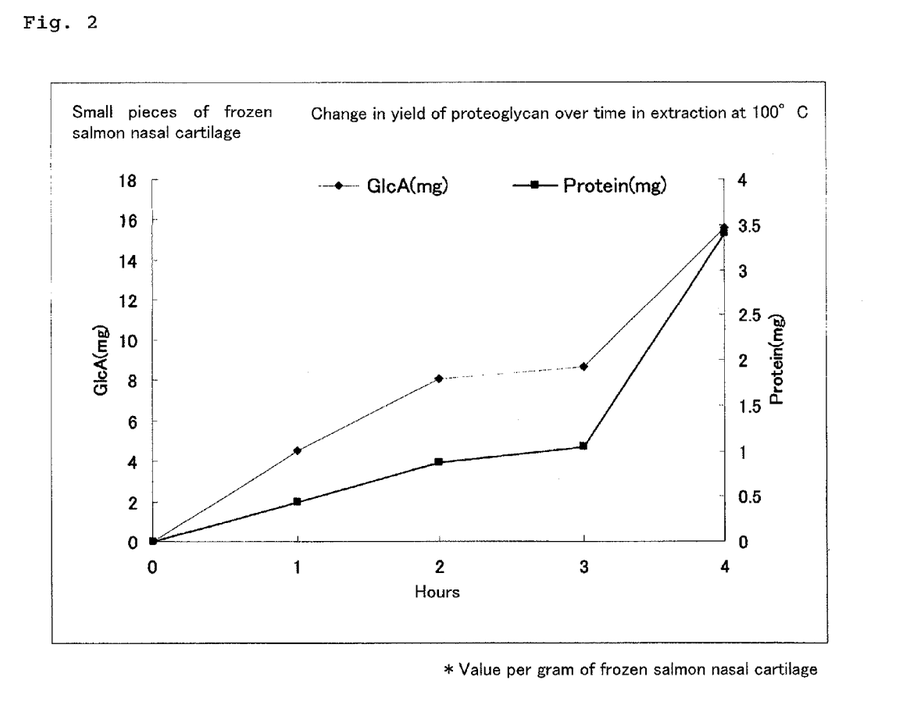
FIG. 2 is a graph showing change in yield of proteoglycan over time when water was added to small pieces of frozen salmon nasal cartilage, and extraction was performed at 100° C.

The present invention is described below in more detail. However, the scope of the invention is not limited to these Examples.
Analysis of Extraction of Proteoglycan from Salmon Nasal Cartilage
Samples Used for Extraction
The following three types ((1) to (3)) of samples derived from salmon nasal cartilage were used for analyzing extraction of proteoglycan. Salmon nasal cartilage used for the analysis was obtained by separating nasal cartilage immediately after thawing a frozen salmon head, washing and defatting the nasal cartilage by running it under water for 6 hours, removing pieces of flesh and the like with tweezers, and washing the nasal cartilage with water by hand.
(1) Frozen Salmon Nasal Cartilage Blocks
Salmon nasal cartilage was stored and frozen in a freezer, and the frozen nasal cartilage was used as a frozen salmon nasal cartilage block. The frozen salmon nasal cartilage block had a size of about 2.5×1.5 cm to about 4.5×2 cm and a weight of about 1.71 g to about 6.91 g. (The average weight of 7 blocks was 3.701 g.), although the size and weight depend on the size of the salmon head used. FIG. 1a shows a photo of a frozen salmon nasal cartilage block.
(2) Small Pieces of Frozen Salmon Nasal Cartilage
Frozen salmon nasal cartilage blocks from item (1) above were placed in a blender and crushed for 10 seconds to prepare small pieces of frozen salmon nasal cartilage. FIG. 1b shows a photo of small pieces of frozen salmon nasal cartilage. Twenty pieces were randomly collected, and the size and the weight of each piece were analyzed. Each piece had a size of about 0.2 cm to about 0.7 cm and a weight of about 0.0116 g to about 0.0890 g. (The average weight of 20 pieces was 0.033 g.) From 100 g of the frozen salmon nasal cartilage blocks, 95.6 g of small pieces of frozen salmon nasal cartilage was obtained.
(3) Defatted Salmon Nasal Cartilage Powder
Proteoglycan composition powder was prepared using frozen salmon nasal cartilage from item (1) above by the method disclosed in Example 1 of Patent Document 1 (JP2009-173702A). This powder was used as defatted salmon nasal cartilage powder. From 100 g of the frozen salmon nasal cartilage blocks, 5.83 g of defatted salmon nasal cartilage powder was obtained. FIG. 1c shows a photo of defatted salmon nasal cartilage powder.
The following is an excerpt from the disclosure of Example 1 of Patent Document 1.
"Frozen salmon nasal cartilage (100 g) was crushed, and an equal volume of tap water at 15° C. was added to the crushed salmon nasal cartilage. The mixture was gently stirred to mix it thoroughly, and the mixture, which was maintained at about 5° C., was immediately centrifuged with a centrifugal separator at 9,000 rpm at 4° C. for 30 minutes to separate lipid and other components including proteoglycan. Three layers were obtained after the centrifugation. The lipid layer in the upper layer and the aqueous layer in the middle layer were removed, and the precipitate was collected. The precipitate was freeze-dried and then pulverized with a centrifugal mill to prepare a water-defatted fine powder. At this stage, some of the fine powder was subjected to ether extraction for measurement of lipid, and it was found that 8.8% lipid remained, that the removal rate was 75.0% when lipid before defatting was defined as 100%, and that the lipid had a faint foul odor. Subsequently, a 10-fold volume of ethanol was added to the water-defatted fine powder to dissolve and extract the lipid with the foul odor. This operation was repeated twice. The ethanol solution was filtered off and the solvent was evaporated to obtain a pale yellow-brown, odorless proteoglycan composition powder. The yield relative to the salmon nasal cartilage was 58.7% (dry basis), and the proteoglycan content was 77.7%. The foul odor of the proteoglycan composition powder completely disappeared."
The "frozen salmon nasal cartilage" of Example 1 of Patent Document 1 corresponds to the "frozen salmon nasal cartilage blocks" described above. The term "dry basis" means a dry mass basis.
Analysis of Proteoglycan Extraction Using Small Pieces of Frozen Salmon Nasal Cartilage
Extraction of proteoglycan was attempted by adding water to small pieces of frozen salmon nasal cartilage prepared as described above in item (2), and heating the mixture at 100° C. More specifically, the analysis was performed as follows. Four samples were prepared. Each sample was prepared by adding 60 mL of distilled water to about 12 g of the small pieces of frozen salmon nasal cartilage. These four samples were heated at 100° C. for 1 hour, 2 hours, 3 hours, and 4 hours, respectively, and each sample was centrifuged with a centrifugal separator at 5,000 rpm at 4° C. for 20 minutes to remove insoluble matter (residue) and collect the supernatant. After the amount of the collected supernatant was measured, the amount of proteoglycan in the supernatant was measured as a uronic acid equivalent by the carbazole-sulfuric acid method. (In tables and figures, uronic acid is represented by the term "GlcA," an abbreviation of glucuronic acid.) In addition, the amount of protein in the collected supernatant was measured by the Bradford method. The results are shown in Table 1. FIG. 2 is a graphical representation of Table 1.

TABLE 1

| Heating time (amount of small pieces (g)) | Amount of liquid (mL) | Per gram of small pieces of frozen salmon nasal cartilage | | GlcA/protein | Residue amount (g) and state |
|---|---|---|---|---|---|
| | | GlcA (mg) | Protein (mg) | | |
| 1 hour (12.261 g) | 31.0 | 4.507 | 0.441 | 10.22 | 33.83 Slightly soft |
| 2 hours (12.322 g) | 40.0 | 8.069 | 0.883 | 9.14 | 28.49 Jelly-like state; shape easily collapses when pressed with a finger |

TABLE 1-continued

| Heating time (amount of small pieces (g)) | Amount of liquid (mL) | Per gram of small pieces of frozen salmon nasal cartilage | | GlcA/protein | Residue amount (g) and state |
| --- | --- | --- | --- | --- | --- |
| | | GlcA (mg) | Protein (mg) | | |
| 3 hours (12.599 g) | 45.5 | 8.636 | 1.039 | 8.31 | 21.79 About to lose its shape |
| 4 hours (12.405 g) | 61.5 | 15.592 | 3.401 | 4.58 | 5.56 No shape, mushy; small amount |

From Table 1 and FIG. 2, it was found that the extraction amount of proteoglycan increases as the heating time is increased. It was also found that heating for more than 3 hours (e.g., 4 hours), in particular, increases the extraction amount of proteoglycan significantly.

Figure 3:
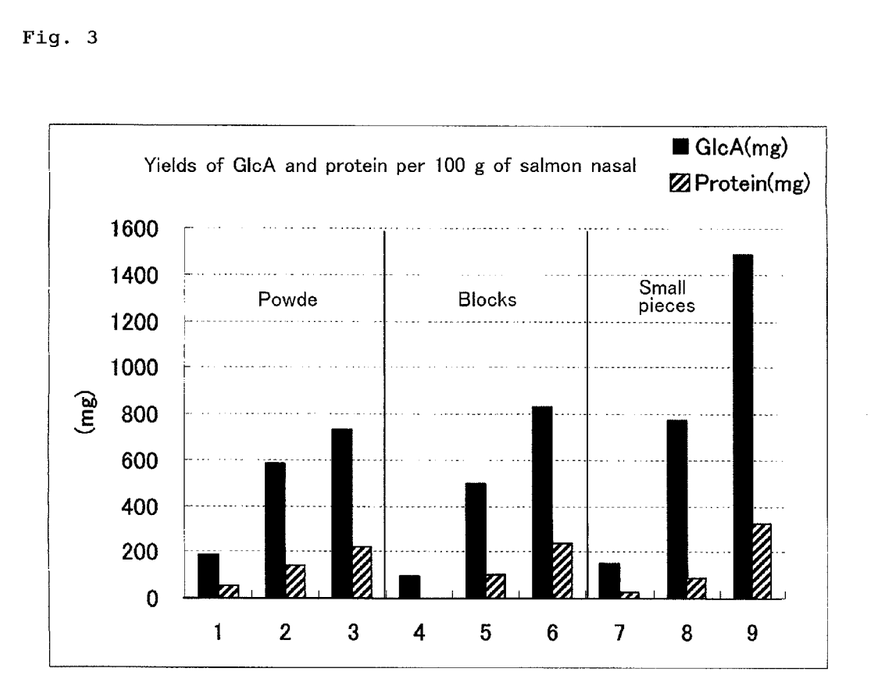
FIG. 3 is a graph showing a comparison of the yields of uronic acid (indicated as "GlcA", an abbreviation for glucuronic acid) and the yields of protein (indicated as "Protein") when proteoglycan is extracted from defatted salmon nasal cartilage powder ("Powder"), frozen salmon nasal cartilage blocks ("Blocks"), or small pieces of frozen salmon nasal cartilage ("Small pieces"). The yields of GlcA and protein are represented in terms of amounts extracted per 100 g of frozen salmon nasal cartilage blocks. The amount of uronic acid reflects the amount of proteoglycan.

Comparison of Small Pieces of Frozen Salmon Nasal Cartilage, Frozen Salmon Nasal Cartilage Blocks, and Defatted Salmon Nasal Cartilage Powder Proteoglycan was also extracted from the frozen salmon nasal cartilage blocks from item (1) and from the defatted salmon nasal cartilage powder from item (3) under the same conditions as for the small pieces of frozen salmon nasal cartilage from item (2) above, and the extraction amounts thereof were compared. The results are shown in Table 2. In Table 2, the amount of extracted proteoglycan and the amount of extracted protein are represented in terms of amounts per 100 g of the frozen salmon nasal cartilage blocks. FIG. 3 is a graphical representation of Table 2. The descriptions of the samples (1 to 9) shown in FIG. 3 correspond to the descriptions in the Graph No. column in Table 2.

TABLE 2

Extraction amounts per 100 g of the Frozen Salmon Nasal Cartilage Blocks (defatted salmon nasal cartilage powder: 5.83 g, small pieces of frozen salmon nasal cartilage: 95.6 g)

| | Graph No. | Heating temperature | Heating time | GlcA (mg) | Protein (mg) | GlcA/protein |
| --- | --- | --- | --- | --- | --- | --- |
| Defatted salmon nasal cartilage powder | 1 | 4° C. | 2 hours | 186.68 | 45.88 | 4.07 |
| | 2 | 100° C. | 2 hours | 581.43 | 136.25 | 4.27 |
| | 3 | 100° C. | 4 hours | 733.15 | 215.30 | 3.41 |
| Frozen salmon nasal cartilage blocks | 4 | 4° C. | 2 hours | 96.90 | — | — |
| | 5 | 100° C. | 2 hours | 499.90 | 96.90 | 5.16 |
| | 6 | 100° C. | 4 hours | 832.10 | 234.85 | 3.54 |
| Small pieces of frozen salmon nasal cartilage | 7 | 4° C. | 2 hours | 150.67 | 18.55 | 8.12 |
| | 8 | 100° C. | 2 hours | 771.40 | 84.41 | 9.14 |
| | 9 | 100° C. | 4 hours | 1490.60 | 325.14 | 4.58 |

From Table 2 and FIG. 3, it was found that the amount of extracted glucuronic acid (reflecting the amount of proteoglycan) significantly increased when the small pieces of frozen salmon nasal cartilage were heated at 100° C. in water for 4 hours. In particular, considering the fact that the amount of uronic acid (reflecting the amount of proteoglycan) contained per 100 g of the salmon nasal cartilage was about 1.6 g (value determined using the carbazole-sulfuric acid method by crushing the nasal cartilage after freeze-drying and by performing extraction with 4 M guanidine hydrochloride/50 mM acetate buffer), the amount of uronic acid extracted at 100° C. for 4 hours from the frozen salmon nasal cartilage blocks was 832 mg (extraction percentage: 52%), whereas the amount of uronic acid extracted at 100° C. for 4 hours from the small pieces of frozen salmon nasal cartilage was 1490.6 mg, and the extraction percentage thereof was 93.2%. Proteoglycan extraction methods with such high extraction efficiency have not been known. It can be said that the present invention has made such high extraction efficacy possible for the first time. Note that since 5.83 g of the defatted salmon nasal cartilage powder was obtained from 100 g of the frozen salmon nasal cartilage blocks, the amount of uronic acid obtained when the defatted salmon nasal cartilage powder was subjected to extraction at 100° C. for 4 hours was 733 mg in terms of the amount per 100 g of the nasal cartilage, and the extraction percentage thereof was 45.8%.

Analysis of Molecular Weight of Proteoglycan

Figure 4:
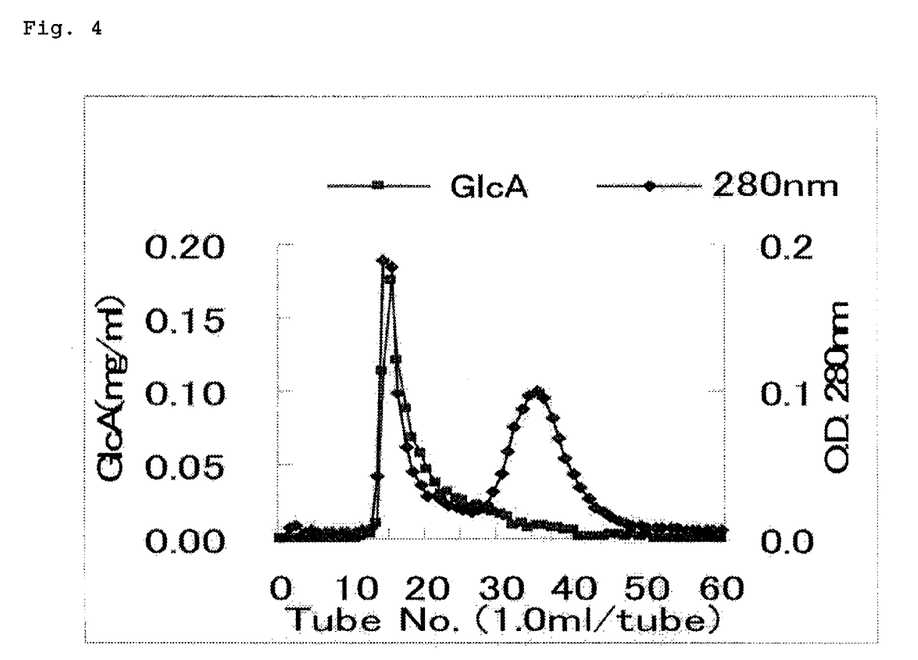
FIG. 4 is a chromatogram drawn based on measurement values obtained by separating collected proteoglycan-containing supernatant extracted from small pieces of frozen salmon nasal cartilage by gel filtration chromatography and measuring the amount of uronic acid (GlcA) in each fraction and absorbency at 280 nm of each fraction.

Proteoglycan extracted as described above was analyzed for molecular weight. More specifically, the analysis was performed as follows. The collected supernatant obtained in "Analysis of Proteoglycan Extraction Using Small Pieces of Frozen Salmon Nasal Cartilage" described above, which contains proteoglycan extracted from the small pieces of frozen salmon nasal cartilage of item (2), was separated into fractions by gel filtration chromatography under the following conditions. The amount of uronic acid (reflecting the amount of proteoglycan) contained in each fraction was quantified by the carbazole-sulfuric acid method. In addition, absorbency at 280 nm of each fraction was measured, and the absorbency was defined as a value reflecting the amount of protein contained therein. Based on these results, a proteoglycan uronic acid amount chromatogram and a proteoglycan protein amount chromatogram were drawn. The results are shown in FIG. 4.

Gel Filtration Chromatography

Column: Sepharose CL-4B packed column (1-cm dia.×38.5 cm column packed with Sepharose CL-4B as a carrier. Sepharose CL-4B is available from, for example, GE Healthcare and other companies. Sepharose CL-4B, CAS registry No. 61970-08-9, is a 4% crosslinked agarose with a particle size of 40 to 165 μm (measured by the laser diffraction scattering method).)

Buffer: 0.1 M phosphate buffer (pH of 7.0, containing 0.2 M NaCl)

Amount of applied sample: about 0.5 mL of the collected supernatant (uronic acid amount: about 1 mg)

Flow rate: about 0.15 mL/min

Amount of fraction: 1 mL/tube

Molecular weight analytical curve: An analytical curve was prepared by subjecting the various dextran molecular weight markers described below to gel filtration chromatography under the same conditions as described above (except that the amount of the applied sample was 1 mg) and quantifying the amount of saccharide (i.e., amount of dextran) contained in each eluted fraction by the phenol-sulfuric acid method.

Dextran Molecular Weight Markers

| | |
| --- | --- |
| Dextran Standard 1,400,000 (Sigma) | 1400 kDa |
| Dextran Standard 670,000 (Sigma) | 670 kDa |
| Dextran Standard 410,000 (Sigma) | 410 kDa |
| Dextran Standard 270,000 (Sigma) | 270 kDa |

Dextran was quantified, specifically, as follows, according to the method described in Hodge, J. E., and Hofreiter, B. T., Method in Carbohydrate Chemistry, 1, 338 (1962).

[1] 500 µl of a sample aqueous solution or a standard monosaccharide (mannose) aqueous solution was placed in a 105×15 mm test tube.
[2] 500 µl of a phenol reagent (5 v/v % aqueous phenol solution) was added thereto, and the mixture was stirred.
[3] 2.5 mL of concentrated sulfuric acid was added thereto, and immediately the mixture was stirred vigorously for 10 seconds.
[4] The mixture was left to stand for 20 minutes or more at room temperature.
[5] The absorbency at 490 nm was measured with a spectrophotometer.

As shown in FIG. 4, the peaks for uronic acid and protein are observed around fraction Nos. 10 to 25 (i.e., peaks for uronic acid and protein overlap). Also from these results, it was confirmed that these fractions contained proteoglycan. This is because it is believed that proteoglycan is contained in a fraction in which both uronic acid and protein are detected, since proteoglycan has a structure in which a number of sugar chains (containing a large amount of uronic acid as constituent sugar) are bonded to a protein (core protein) that serves as a core. It was also believed that from the molecular weight analytical curve, the molecular weight of the component contained in fraction No. 20 was about 900,000 ($90 \times 10^4$), and the molecular weight of the component contained in fraction No. 30 was about 150,000 ($15 \times 10^4$). Accordingly, it was found that the collected supernatant obtained from the small pieces of frozen salmon nasal cartilage contained high-molecular-weight proteoglycan having a molecular weight of not less than about 900,000 ($90 \times 10^4$). In the figures, the fraction No. is indicated as "Tube No.", and these are synonymous.

Figure 5:
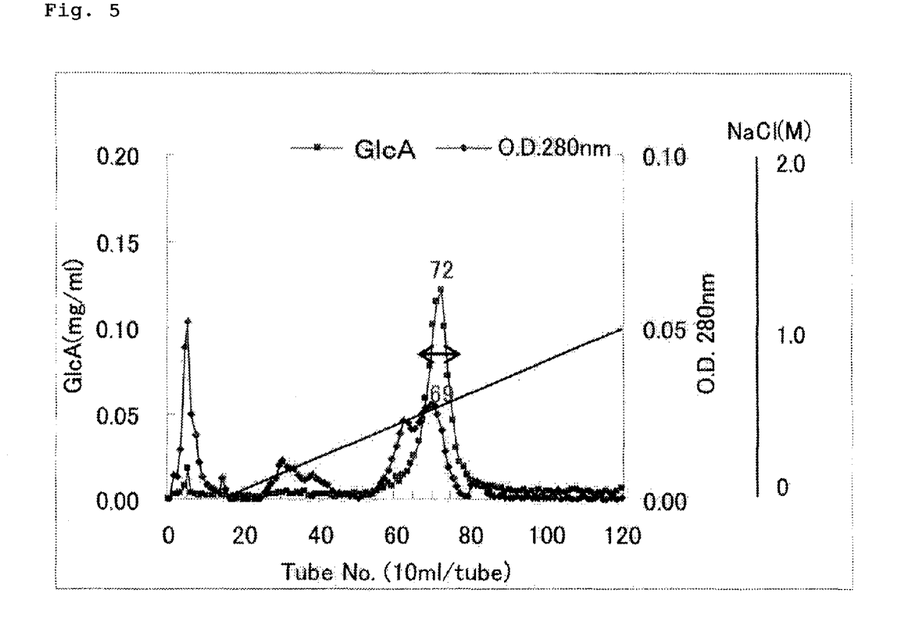
FIG. 5 is a chromatogram drawn based on measurement values obtained by separating collected proteoglycan-containing supernatant extracted from small pieces of frozen salmon nasal cartilage by anion exchange chromatography and measuring the amount of uronic acid (GlcA) in each fraction and absorbency at 280 nm of each fraction.

In addition, the collected proteoglycan-containing supernatant extracted from the small pieces of frozen salmon nasal cartilage was separated into fractions by anion exchange chromatography under the following conditions, and a proteoglycan uronic acid amount chromatogram and a proteoglycan protein amount chromatogram were drawn in the same manner as described above. It was found that the peak for uronic acid and the peak for protein overlapped (FIG. 5, left-right arrow). This also provides evidence that proteoglycan was contained in the collected supernatant.

Anion Exchange Chromatography
Column: DEAE Sephacel packed column (2.5-cm dia.×10 cm column packed with DEAE (diethylaminoethyl) Sephacel as a carrier. DEAE Sephacel is available from, for example, GE Healthcare and other companies.)
Buffer: 7 M Urea/50 mM Tris-HCl buffer (pH of 7.4) (Linear gradient elution is performed with 0.1 M NaCl.)
Amount of fraction: 10 mL/tube

The invention claimed is:

1. A method for extracting proteoglycan from fish cartilage, comprising the step of (A) heating small pieces of frozen fish cartilage in water, wherein each small piece of frozen fish cartilage is 0.001 to 0.5 g, and the temperature of the water used in the heating in Step (A) is not less than 80° C., and wherein the heating in step (A) is performed for more than 3 hours.

2. The method according to claim 1, wherein the small pieces of frozen fish cartilage are obtained by freezing fish cartilage and then pulverizing the frozen fish cartilage.

3. The method according to claim 2, wherein the fish cartilage is defatted fish nasal cartilage.

4. The method according to claim 1, wherein the extracted proteoglycan contains proteoglycan having a molecular weight of not less than 900,000 ($90 \times 10^4$) Daltons.

5. The method according to claim 1, wherein a mass ratio of all the small pieces of frozen fish cartilage to water is 1:1 to 1:10.

6. The method according to claim 1, wherein the heating in Step (A) is continued until the mass of a residue collected after the heating is equal to or less than the mass of the heated small pieces of frozen fish cartilage.

7. The method according to claim 6, wherein the residue collected after the heating is a precipitate obtained by centrifugation at 5000 rpm, 4° C., for 20 minutes.

8. A method for increasing efficiency in proteoglycan extraction from fish cartilage, comprising the step of heating small pieces of frozen fish cartilage in water, wherein each small piece of frozen fish cartilage is 0.001 to 0.5 g, and the temperature of the water used in the step is not less than 80° C., and wherein the step of heating is performed for more than 3 hours.

* * * * *